United States Patent
Rishton et al.

[11] Patent Number: 6,015,391
[45] Date of Patent: Jan. 18, 2000

[54] BIOPSY NEEDLE STRUCTURE

[75] Inventors: Michael Lyne Rishton; Harold Leonard Newman, both of Reading, Mass.; Alec Goldenberg, New York, N.Y.

[73] Assignee: Medsol, Corp., New York, N.Y.

[21] Appl. No.: 09/167,230

[22] Filed: Oct. 6, 1998

[51] Int. Cl.⁷ .................................................. A61B 10/00
[52] U.S. Cl. ........................ 600/567; 600/562; 600/564
[58] Field of Search .................................. 600/562, 564, 600/566, 567; 606/167, 170

[56] References Cited

U.S. PATENT DOCUMENTS

| | | | |
|---|---|---|---|
| 3,605,721 | 9/1971 | Hallac | 128/2 B |
| 4,461,305 | 7/1984 | Cibley | 128/754 |
| 4,576,162 | 3/1986 | McCorkle | 128/303 |
| 4,651,752 | 3/1987 | Fuerst | 128/754 |
| 4,653,496 | 3/1987 | Bundy et al. | 600/564 |
| 4,785,826 | 11/1988 | Ward | 128/754 |
| 4,926,877 | 5/1990 | Bookwalter | 600/567 |
| 4,932,417 | 6/1990 | Ott | 600/562 |
| 4,935,025 | 6/1990 | Bundy et al. | 600/564 |
| 5,133,360 | 7/1992 | Spears | 600/567 |
| 5,148,813 | 9/1992 | Bucalo | 128/754 |
| 5,267,572 | 12/1993 | Bucalo | 600/567 |
| 5,522,398 | 6/1996 | Goldenberg et al. | 600/567 |
| 5,634,473 | 6/1997 | Goldenberg et al. | 128/754 |
| 5,762,069 | 6/1998 | Kelleher et al. | 600/564 |
| 5,823,971 | 10/1998 | Robinson et al. | 600/567 |
| 5,919,202 | 7/1999 | Yoon | 606/170 |

*Primary Examiner*—Cary O'Connor
*Assistant Examiner*—Charles Marmor, II
*Attorney, Agent, or Firm*—Darby & Darby

[57] ABSTRACT

An improved biopsy needle having an outer cannula, an inner tube, and a stylet. A snare in the form of a coil is provided between the distal ends of the outer cannula and the inner tube. The coil is coupled to a sleeve affixed to the inner surface of the outer cannula using axially directed coupling elements. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

14 Claims, 6 Drawing Sheets

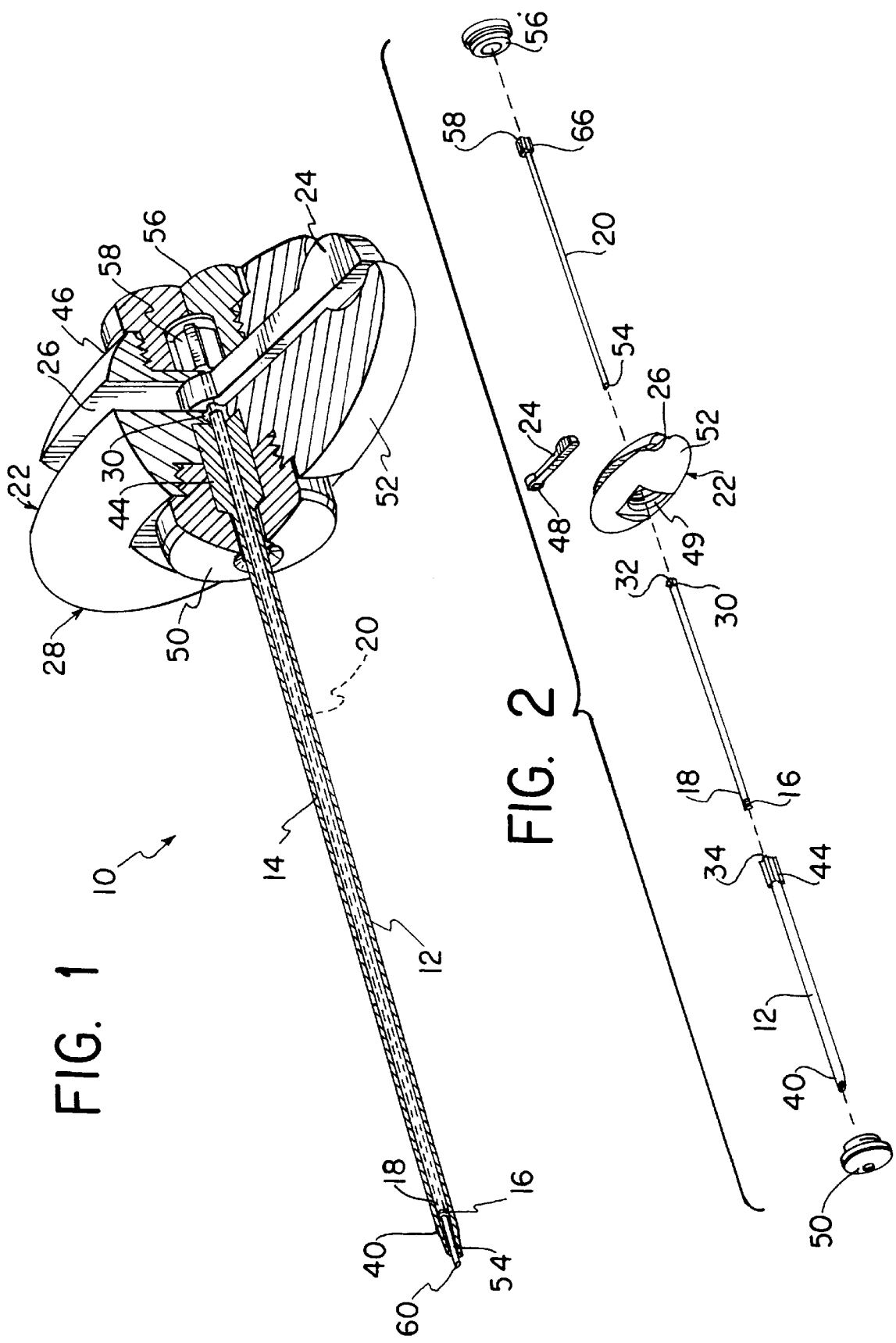

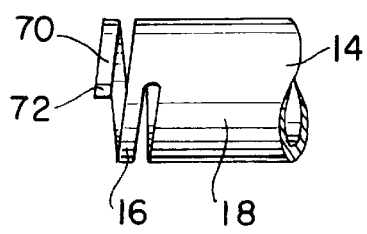
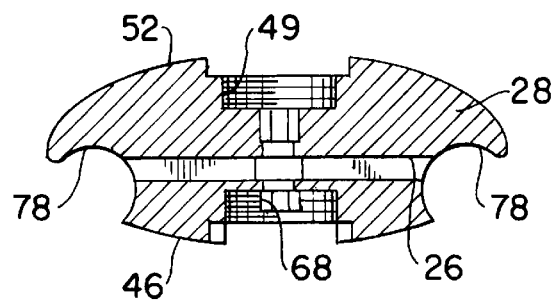
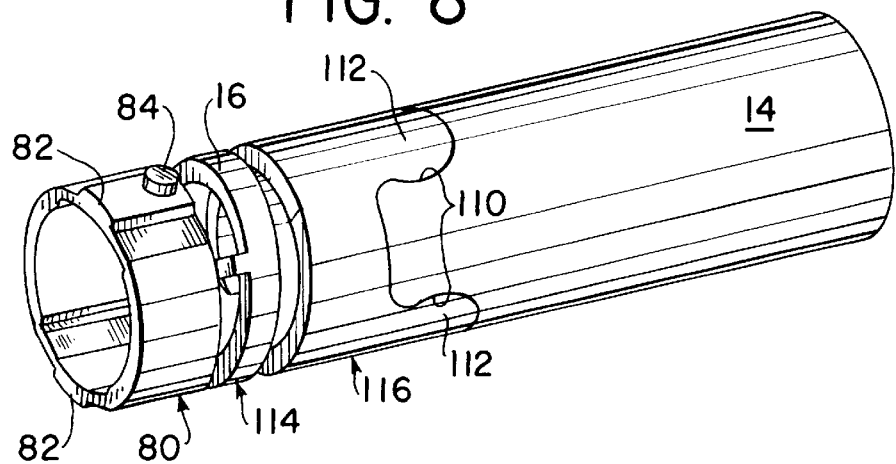
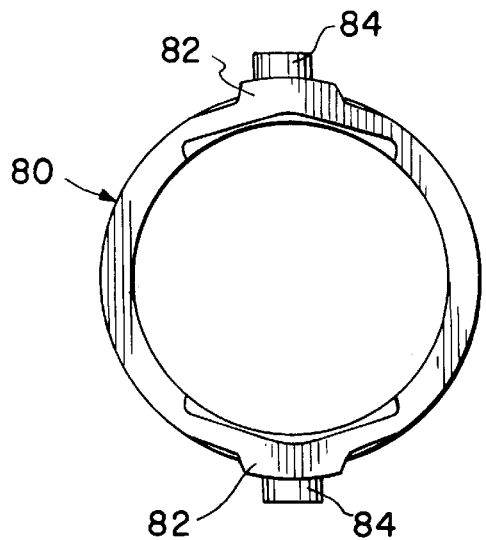

6,015,391

BIOPSY NEEDLE STRUCTURE

FIELD OF THE INVENTION

This invention relates generally to a surgical instrument, known variously as a biopsy needle or cannula that is used to gather tissue, such as bone narrow, from living persons or animals for pathological study. More specifically, the invention relates to a biopsy needle structure which couples a tissue snare to the cannula.

BACKGROUND OF THE INVENTION

For various medical reasons, such as diagnostic tests or the determination of suitability as a tissue donor, it is often necessary for a physician to obtain a sample of a patient's body tissue. In particular, bone marrow is frequently retrieved for later pathological study as described in U.S. Pat. No. 5,634,473, the entirety of which is hereby incorporated by reference as if set forth herein. The U.S. Pat. No. '473 discloses a biopsy needle assembly which includes a snare that operates to sever and/or retain a sample. The snare is coupled to the cannula with radially directed coupling elements. The radially directed coupling elements include a radially projecting tab which is received within an aperture formed in a sidewall of the cannula.

SUMMARY OF THE INVENTION

The present invention concerns improvements in biopsy needle design of the type having a snare in the form of a coil provided between the distal ends of an outer cannula and an inner tube. The coil is coupled to a sleeve affixed to the inner surface of the outer cannula using axially directed coupling elements. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

In accordance with one aspect of the invention, an improved biopsy needle for removal of tissue from a patient is disclosed, the needle including an outer tube, an inner tube and a snare having first and second ends. A first end of the snare is coupled to the inner tube and a second end of the snare is coupled to the outer tube. The snare moves between first and second positions by rotation of the inner tube with respect to the outer tube. The second end of the snare has an axially directed coupling element which is either a projection or a slot. Affixed to the outer tube is the other of the projection and slot which is arranged to engage the second end of the snare.

In accordance with another aspect of the present invention, a biopsy needle comprises an outer tube having a distal end and an inner tube extending within said outer tube. The inner tube has at one end a portion (e.g., a snare or other structure) which increases and decreases in diameter with rotation of the inner tube relative to the outer tube. At the distal end of the portion and at the distal end of the outer tube, there are corresponding axially directed coupling elements which engage one another.

Other features of the invention include a keyed slot at a distal end of the inner tube which receives a correspondingly shaped first end of the snare, for example, as a result of an injection molding process step. Also, the snare preferably includes a helical portion having an axial length that is shorter than the length of the projection. Further features are understood from the following detailed description which includes a description of the best mode for practicing the invention.

BRIEF DESCRIPTION OF THE DRAWINGS

Other objects, advantages and embodiments than those described above will become apparent to those skilled in the art upon reading the following detailed description in conjunction with a review of the appended drawings, in which:

FIG. 1 is a perspective view of a biopsy needle;

FIG. 2 is an exploded view, with parts shown in section, of the biopsy needle of FIG. 1;

FIG. 6 is a side view of the inner tube;

FIG. 7 is a cross-section view through the handle piece of the biopsy needle;

FIG. 8 is a perspective view of the distal end of a second arrangement for a biopsy needle;

FIG. 9 is an end view of the distal end of the second arrangement;

DETAILED DESCRIPTION

Figure 3A:
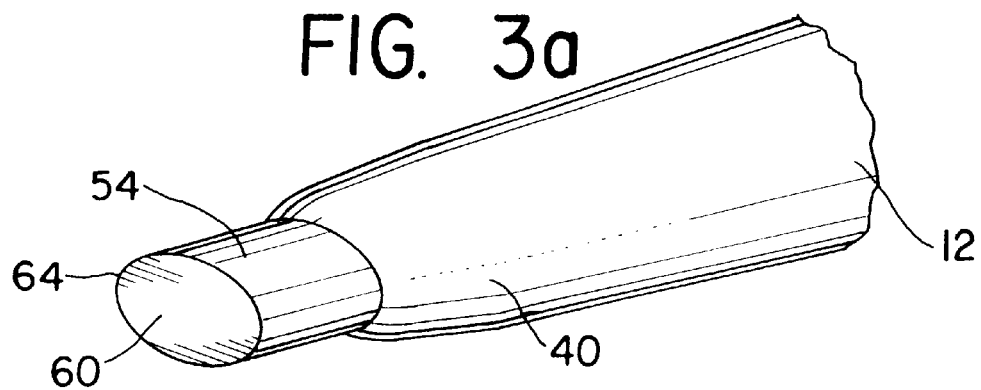
FIGS. 3a–3e are detail perspective views on an enlarged scale, of the distal end of the biopsy needle illustrating the function of various components during operation of the biopsy needle.

Referring now to FIGS. 1 and 2, biopsy needle 10 has an outer cannula 12, an inner tube 14 with a cylindrical or helical snare 16 at its distal end 18, a stylet 20, and a handle assembly 22. The handle assembly 22 forms no part of the present invention, and the following description is of the handle described in the aforesaid U.S. Pat. No. 5,634,473. In FIG. 2, the assembly of the present biopsy needle 10 is shown in an exploded view.

Figure 4:
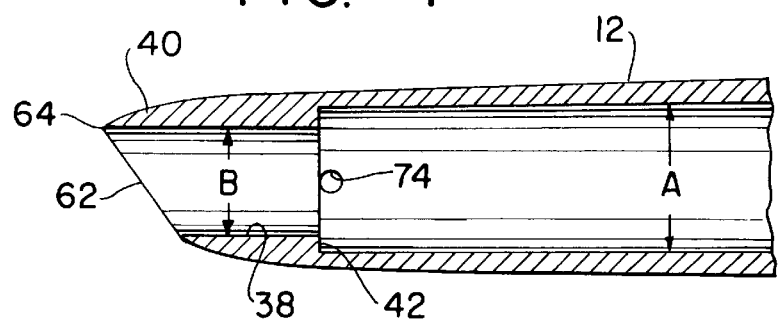
FIG. 4 is a cross-sectional view of the distal end of the outer cannula.
Figure 12:
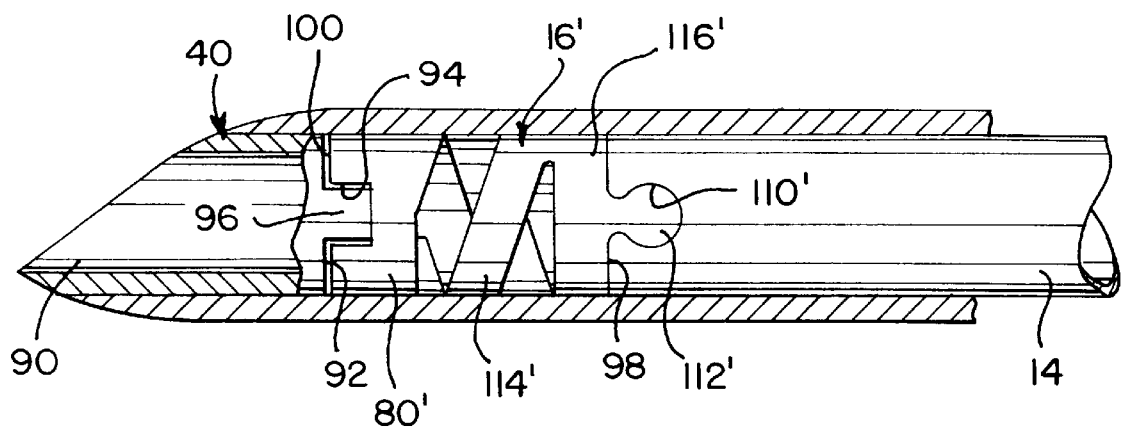
FIG. 12 is a side view, particularly in section, of a biopsy needle structure of the present invention showing axially directed coupling elements between the snare and the cannula.

As part of the handle assembly 22, a lever 24 is mounted for rotation in a corresponding groove 26 within a handle piece 28. Upon rotation, the lever 24 actuates the snare 16 within the outer cannula 12 without any movement of the outer cannula 12 relative to the patient (not shown). The operation of this lever 24 is described more fully below. The inner tube 14 has a snare 16 at its distal end 18 and a gear 30 is mounted on its proximal end 32. The inner tube 14 is inserted into the proximal end 34 of the outer cannula 12 so that the gear 30 protrudes from the proximal end 34. As can be seen in FIG. 4, the interior of the outer cannula 12 has a constant inner diameter A along most of its length, with a portion 38 having a smaller inner diameter B at its distal tip 40. The constricted diameter B is preferably achieved by affixing coaxial sleeve 90 within the distal tip 40, as shown in FIG. 12.

Preferably, the narrow inner diameter B at the distal tip 40 is substantially equal to the inner diameter C (FIG. 3c) of the inner tube 14 so that there will be no ridge or lip within the instrument to impede tissue entering the instrument. The inner tube 14 is inserted in cannula 12 until the snare 16 reaches a shoulder 42 provided on the interior of the outer cannula 12 at the position where the diameter changes (see FIGS. 3b and 3c) or the proximal margin or shoulder 92 of the sleeve 90 (FIG. 12).

As best seen in FIG. 1, with the gear 30 extending proximal of the cannula's anchor 44, the cannula and snare assembly are attached to the handle piece 28 at the proximal facing side 46 of the handle 22. The gear 30 of the snare 16 is inserted into a complementary hole 48 in the lever while the anchor 44 of the outer cannula 12 mates with a complementary hole 49 in the handle piece 28. Thus, when the lever 24 is rotated within its groove 26 with respect to the handle piece 28, the inner tube 14 will rotate with respect to the outer cannula 12. A cannula cap 50 is assembled onto the distal tip 40 of the cannula and threadedly engaged to the forward facing end 52 of the handle piece 28. The stylet 20 is inserted into the proximal end 32 of the inner tube until a distal tip portion 54 of the stylet extends beyond the distal tip 40 of the cannula. A stylet cap 56 can then be threadedly engaged to the proximal facing side 46 of the handle piece, covering the proximal end 58 of the stylet to prevent it from moving proximally within the inner tube 14.

As can be seen in FIG. 3a, both the distal ends 40, 54 of the stylet 20 and the outer cannula preferably have sloped end faces 60, 62 although it is not necessary. This improves the cutting action of the both the stylet and the outer cannula by providing sharp leading edges 64. In this position, the stop 66 at the proximal end 58 of the stylet preferably mates with a complementary indent 68 in the handle piece 28 to maintain the rotational orientation of the stylet 20 with respect to the outer cannula 12 such that the slopes of the two distal ends 40, 54 are approximately parallel. This is the configuration that would be used for inserting the biopsy needle 10 into the patient and through the bone into the softer bone marrow tissue within.

Figure 3B:
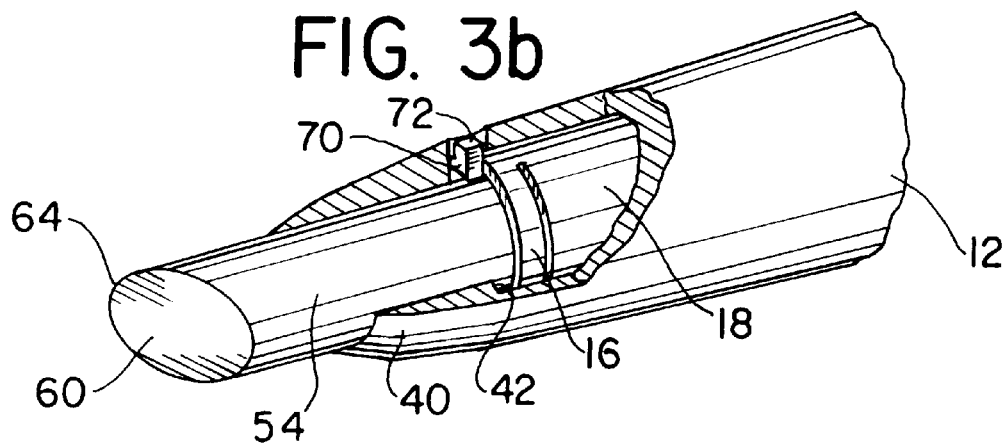
Figure 3C:
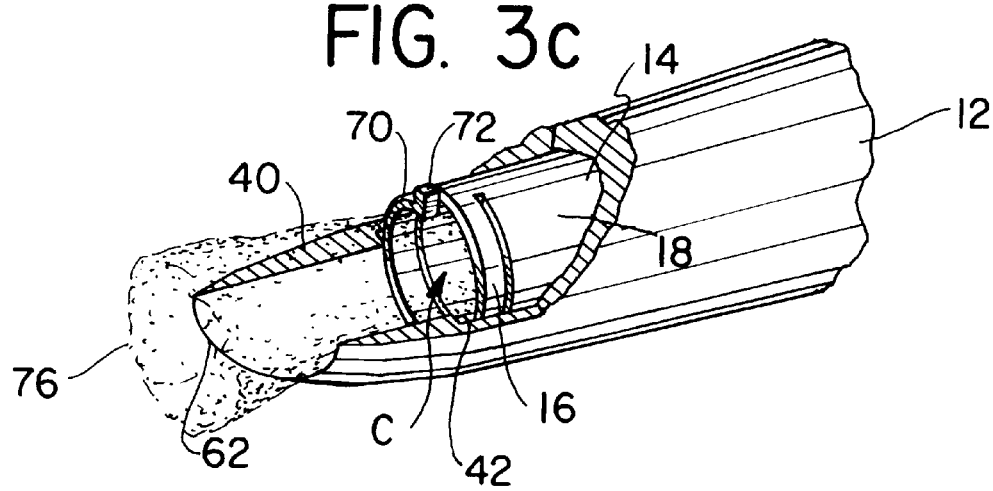

As can be seen in FIG. 3b, which is a partial cutaway view, the free end 70 of the coil snare 16 includes a radial tab 72 that engages or is attached to a hole 74 (FIG. 4) suitably positioned on the interior surface of the outer cannula 12. This hole 74 may extend through the entire wall of the outer cannula. If desired, the radial tab 72 can be adhered to the hole 74 in the outer cannula through the use of adhesives, welding, or any known attachment process. As described below in connection with FIG.12, a more preferred coupling uses axially directed coupling elements. After the needle 10 is inserted into the marrow, the stylet 20 is withdrawn proximally without any movement of the outer cannula 12 with respect to the patient, minimizing discomfort. As can be seen in FIG. 3c, marrow tissue may now enter the passageway within the outer cannula 12 through the distal end 40 of the outer cannula and can enter the inner passageway of the inner tube 14, preferably to a position proximal of the snare 16.

Figure 3D:
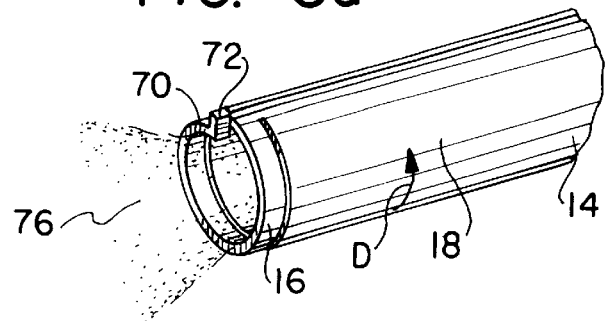
Figure 3E:
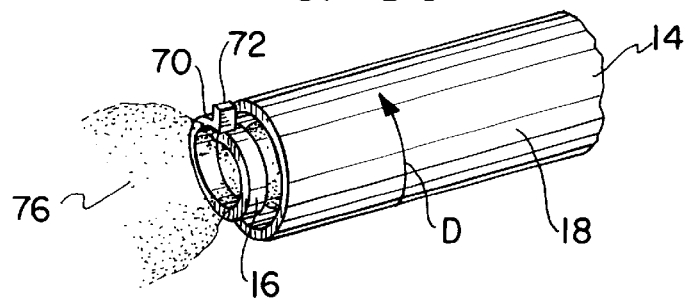

To operate the snare 16, i.e. to cause cutting and/or holding of the biopsy piece 76 within the inner tube 14, the lever 24 attached to the proximal end 32 of the inner tube is rotated in the direction of arrow D as seen in FIGS. 3d–3e. Of course, the snare 16 can be designed such that rotation in the opposite direction causes the same effect. With full rotation (180.°) of the lever 24, the inner tube 14 and snare 16 achieve a position similar to that shown in FIG. 3e, in which the inner tube 14 has been rotated approximately 180.°. Since the free end 70 of the snare is fixed to the outer cannula 12, the result of the rotation is that the coil of the snare 16 will tighten so that the cross-sectional area through the snare 16 is approximately less than a third of the area when in the open configuration. It is also contemplated that any decrease, even a slight decrease, in the cross-sectional area of the snare will cause pressure on the biopsy piece 76. Therefore, while the current amount of rotation is preferred, it is not necessary for the proper functioning of the present invention.

Figure 5:
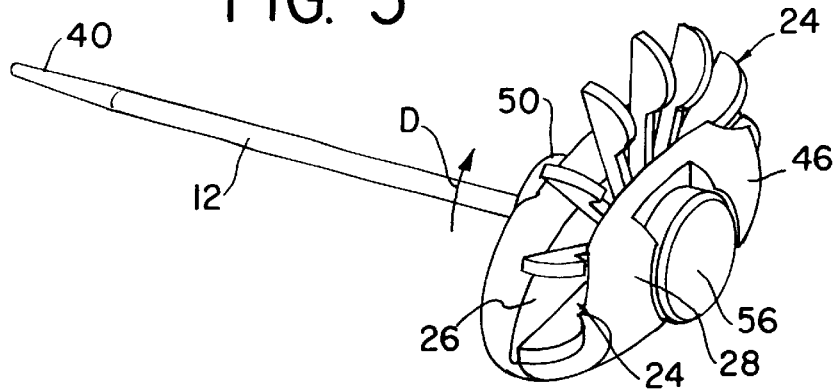
FIG. 5 is a perspective view of the biopsy needle showing operation by a physician.

As seen in FIG. 5, movement of the lever 24 can be independent of any movement of the handle piece 28 or the outer cannula 12. Therefore, the outer cannula 12, which is in direct contact with the patient while the sample is taken, can remain substantially stationary. There is little or no discomfort at this step of the procedure, where previously this had been one of the more uncomfortable steps.

With the tightening of the snare 16, there is a high probability that the biopsy piece 76 will remain in the needle 10 as the needle is removed. If the tightening of the snare 16 does not immediately cause the biopsy piece 76 to be cut, it will be significantly squeezed and/or notched, such that rearward motion of the needle 10, which causes rearward pressure on any biopsy piece 76 proximal of the snare 16, will cause material proximal of the snare 16 to detach from material that is distal of the snare.

As can be seen in FIG. 7, the handle 22 includes several features designed for ease of use of the physician and ease of manufacture and construction. The handle piece 28 includes a groove 26 that receives the lever 24 while permitting its rotation. The groove 26 has two notches 78 that generally protect the lever 24 from any accidental contact with the physician when in either the full-open or full-closed positions, but allow access to the lever. Further, the holes in the handle piece 28 that receive the anchor 44 of the outer cannula and the stop 66 of the stylet have shapes that are complementary to the anchor or stop, in order to prevent rotation of those two components with respect to the handle, as previously discussed. The proximal and distal facing sides 46, 52 of the handle piece are also provided with threaded regions for receiving the cannula and stylet caps 50, 56.

Once the biopsy needle 10 has been used and the captured material has been ejected through either the proximal or distal ends of the inner tube, the biopsy needle 10 can be sterilized for its next use. If necessary, the entire biopsy needle can be disassembled, although the tab 72 at the free end of the snare must be disengaged from the hole 74 in the outer cannula. This can be accomplished with any small tool pushed through hole 74. If the free end 70 of the snare is permanently adhered to the outer cannula 12, it then may be necessary to sterilize the outer cannula and inner tube as a single unit. However, due to the small number of parts and relative ease and low cost construction of the present needle, it is also contemplated that such a device is easily disposable.

Thus, it can be seen that a low cost, simply-manufactured biopsy needle will attain improved results over known devices, not only in the success rate of the marrow extraction procedures, but also a marked increase in patient comfort throughout the procedure. One desirable side benefit of this increased comfort might be increased participation in bone marrow donor programs for transplant candidates.

FIGS. 8–11 illustrate an arrangement in which the coil snare 16 is provided with a cylindrical member 80 at its distal end. Although it is preferred that the cylindrical member be integral with the free end of the coil snare 16, the cylindrical member 80 may alternatively be securely attached to the free end of the coil snare 16.

Figure 10:
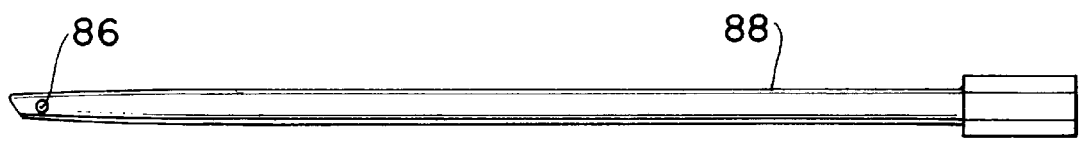
FIG. 10 is a left side view of the outer cannula, the right side being a mirror image thereof.
Figure 11:
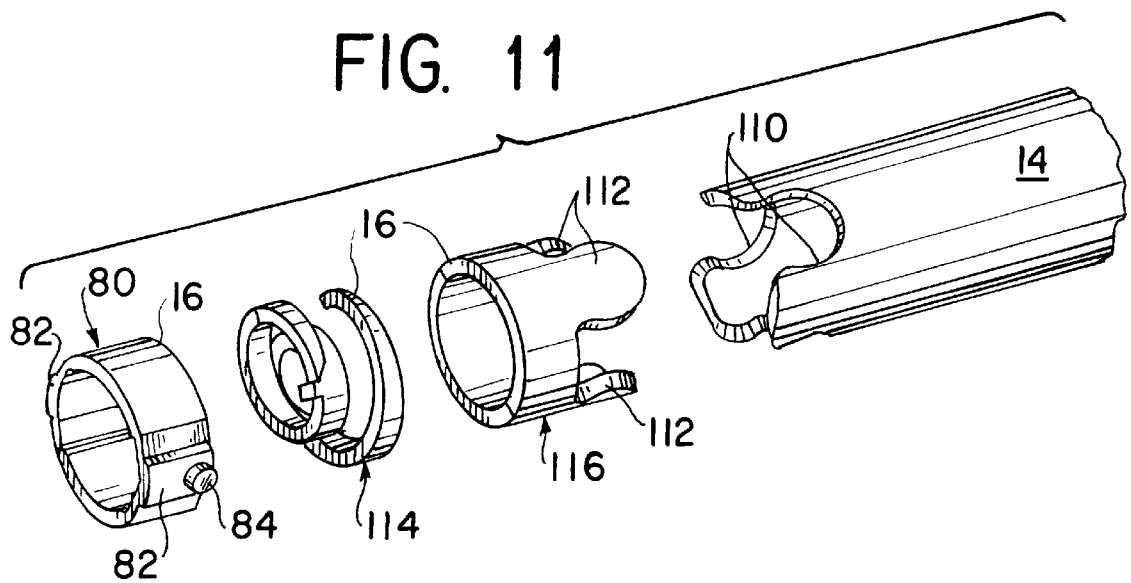
FIG. 11 is an exploded view of the distal end of the second arrangement.

The cylindrical member 80 is provided with two equidistantly spaced raised rectangular members 82 positioned about the circumference of the cylindrical member 80. As more clearly shown in FIG. 9, each rectangular member 82 includes a tab 84 which engages or is secured in a hole 86 on the interior surface of the outer cannula 88 (FIG. 10). Each hole 86 is sized and positioned to accept a tab 84 that may extend through the entire wall of the outer cannula 12. Each tab 84 may be secured to outer cannula 88 in the same manner as described in connection with tab 72 of FIG. 3b. The cylindrical member 80 provides increased strength to the free end of the coil snare 16 without changing the manner in which the present invention operates. Referring again to FIGS. 8 and 11, the coil snare 16 is illustrated as a member separate from, but connected to the inner tube 14 rather than integral with the inner tube 14 as shown in FIGS. 3a–3e. FIG. 11 shows an exploded view of the distal end of the inner tube 14 and coil snare 16 clearly illustrating the manner in which they are connected. The distal end of inner tube 14 includes three equidistantly spaced curved recesses 110 for matingly receiving three equidistantly spaced curved male portions 112 integral with the coil snare 16. Formed in this manner, the inner tube 14 and the coil snare 16 may be made of two different materials, with the inner tube 14 preferably made of a rigid material while the coil snare 16 is preferably made of a flexible plastic material and then the coil snare 16 may be permanently adhered to the inner tube 14 using an adhesive.

Also illustrated in FIG. 11 is an exploded view of the coil snare 16. The coil snare 16 comprises three preferably integral portions, the cylindrical portion 80, a helical portion 114 (shown in its actuated or reduced diameter condition) and a base portion 116 which carries the male portions 112. As is evident from the figure, the helical portion 114 operates in the same manner as the coil snare described in connection with FIGS. 3a–3e.

Figure 13:
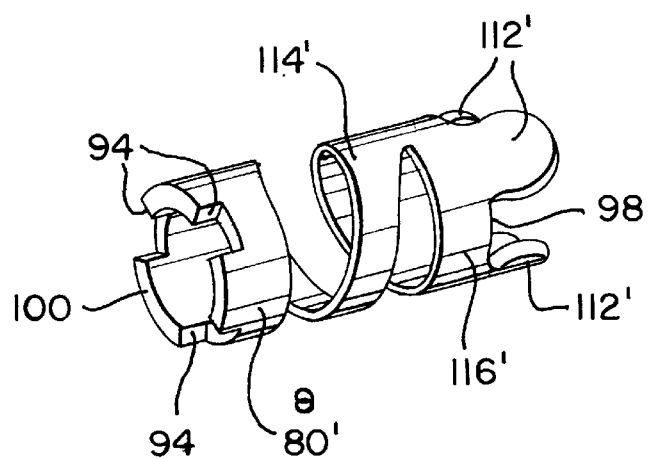
FIG. 13 is an exploded view of the biopsy needle structure of the present invention.

With reference now to FIGS. 12 and 13, a biopsy needle structure in accordance with the invention has the snare 16' engaged to the cannula 12' through corresponding, axially directed coupling elements 94, 96. As in the arrangement of FIGS. 8–11, the snare 16' preferably includes a cylindrical member 80', a helical portion 114', and a base portion 116', wherein the base portion supports one or more male portions 112' from a proximal face 98 thereof. The snare 16' is preferably a unitary piece of resiliently deformable material such as polyurethane which is affixed to the inner tube 14 by injection molding the polyurethane onto the distal end of the tube. The curved recesses 110' define a key-hole slot which securely retains the base portion 116' at a first end of the molded snare 16'. The recesses 110' are preferably curved to maximize surface area contact, but may be dovetail or otherwise shaped to prevent movement (e.g. axial movement) of the snare 16' relative to the inner tube 14. Preferably, three male portions 112' are provided along with three recesses 110'.

An opposing, second end of the snare 16' is coupled to the cannula 14 by notches 94 within a distal face 100 of the snare 16'. The notches 94 engage axially directed tabs or projections 96 provided at the proximal margin 92 of the sleeve 90. Preferably, three tabs 96 are provided to ensure that the coil 114' does not slip due to applied torque. The sleeve 90 is preferably affixed to the cannula by brazing, but can be soldered, welded, crimped or adhesively secured, as understood by those of skill in the art.

The tabs 96 preferably extend axially for a length which is about or more than the axial length of the helical portion 114'. This better ensures that the tabs 96 will not be unseated from within the slots 94, for example, were a sample or bone mass to compress the coil in an axial direction and partially retract the tabs from their seat. By forming the tabs 96 longer than the axial length of the helical portion 114', the tabs will not be unseated from the slots 94 during use. Preferably, the slots have a depth which corresponds to the length of the tabs to ensure good transfer of torque between the distal end of the snare 16' and the outer cannula 12.

The axially directed coupling elements 94, 96 provide a simple biopsy needle structure for assembling and coupling the snare and inner tube to the cannula. Importantly, the axially directed coupling elements permit the snare 16' to readily engage one another upon assembly of the inner tube and outer tube or cannula 14, 12, respectively.

Preferably, the notches 94 are provided within the proximal margin of the sleeve 90 and tabs extend axially from the distal face 100 of the snare 16'. Likewise features of the arrangements described in connection with FIGS. 1–11 can be used with the axially directed coupling elements 94, 96 of the present invention, instead of radially directed tabs 72, 84 and holes 74, 86.

While the embodiments shown and described above are fully capable of achieving the objects and advantages of the present invention, it is to be understood that these embodiments are shown and described solely for the purposes of illustration and not for limitation. Accordingly many additions, modifications, and substitutions are possible without departing from the scope and spirit of the invention as defined in the accompanying claims.

We claim:

1. A biopsy needle for removal of tissue from a patient of the type including an outer tube, an inner tube and a snare having first and second ends, the first snare end being coupled to said inner tube and said second snare end being coupled to said outer tube, said snare being movable between first and second positions by rotation of said inner tube with respect to said outer tube, wherein the improvement comprises:

an axially directed coupling element at said second snare end, said axially directed coupling element being one of a projection and slot;

the other of said projection and said slot being associated with said outer tube and arranged to engage said second snare end.

2. The biopsy needle as in claim 1, wherein said second snare end is a ring which supports said axially directed coupling element.

3. The biopsy needle as in claim 1, further comprising a sleeve affixed to a distal end of said outer tube, the other of said projection and said slot being supported on said sleeve.

4. The biopsy needle as in claim 3, wherein said outer tube has a lumen and wherein said sleeve is disposed within the lumen.

5. The biopsy needle as in claim 1, wherein the inner tube has a keyed slot at a distal end thereof and wherein said first snare end is shaped to correspond to the keyed slot.

6. The biopsy needle as in claim 5, wherein said snare and said first snare end are formed and coupled to the inner tube by an injection molding process step.

7. The biopsy needle as in claim 1, wherein said snare includes a helical portion having an axial length that is shorter than the length of said projection.

8. A biopsy needle, comprising:

an outer tube having a distal end;

an inner tube extending within said outer tube, said inner tube having at one end a portion which increases and decreases in diameter with rotation of said inner tube relative to said outer tube, said portion of said inner tube and said distal end of said outer tube each including corresponding axial directed coupling elements which engage one another.

9. The biopsy needle as in claim 8, wherein said portion has a ring which supports said axially directed coupling element of said portion.

10. The biopsy needle as in claim 8, further comprising a sleeve affixed to the distal end of said outer tube, said sleeve supporting said axially directed coupling element of said outer tube.

11. The biopsy needle as in claim 10, wherein said outer tube has a lumen and said sleeve is disposed within said lumen.

12. The biopsy needle as in claim 8, wherein said inner tube has a keyed slot at said one end and wherein said portion has a first end which is shaped to correspond to the keyed slot.

13. The biopsy needle as in claim 11, wherein said portion and said first end of said portion are formed and coupled to said inner tube by an injection molding process step.

14. The biopsy needle as in claim 8, wherein said portion is helically shaped and wherein said corresponding axial directed coupling elements comprise a projection and a slot, wherein said helically shaped portion has an axial length that is shorter than the length of said projection.

* * * * *

Disclaimer

6,015,391 — Michael Lyne Rishton; Harold Leonard Newman, both of Reading, Mass.; Alec Goldenberg, New York, N.Y., BIOPSY NEEDLE STRUCTURE. Patent dated January 18, 2000. Disclaimer filed July 2, 2007, by the assignee, Medsol, Corp.

Hereby enters this disclaimer to claims 1-14, of said patent.

*(Official Gazette November 6, 2007)*